(12) United States Patent
Nagata et al.

(10) Patent No.: US 8,672,955 B2
(45) Date of Patent: Mar. 18, 2014

(54) MEDICAL SUTURING DEVICE

(75) Inventors: Katsuki Nagata, Shizuoka (JP); Ichiro Kitani, Shizuoka (JP); Shigeaki Funamura, Shizuoka (JP); Yoshihiro Wada, Shizuoka (JP)

(73) Assignee: Covidien LP, Mansfield, MA (US)

( * ) Notice: Subject to any disclaimer, the term of this patent is extended or adjusted under 35 U.S.C. 154(b) by 124 days.

(21) Appl. No.: 12/826,114

(22) Filed: Jun. 29, 2010

(65) Prior Publication Data

US 2010/0305586 A1    Dec. 2, 2010

Related U.S. Application Data

(63) Continuation of application No. 11/613,937, filed on Dec. 20, 2006, now abandoned.

(30) Foreign Application Priority Data

Dec. 26, 2005   (JP) ................................. 2005-371754

(51) Int. Cl.
    *A61B 17/04*   (2006.01)
(52) U.S. Cl.
    USPC ............................ 606/144; 606/139; 606/148
(58) Field of Classification Search
    USPC ................ 606/139, 144, 148, 232; 623/23.72
    See application file for complete search history.

(56) References Cited

U.S. PATENT DOCUMENTS

| | | |
|---|---|---|
| 2,012,776 A | 8/1935 | Roeder |
| 4,775,121 A | 10/1988 | Carty |
| 4,935,027 A | 6/1990 | Yoon |
| 5,037,433 A | 8/1991 | Wilk et al. |
| 5,052,396 A | 10/1991 | Wedel et al. |
| 5,100,387 A | 3/1992 | Ng |
| 5,123,914 A | 6/1992 | Cope |
| 5,226,892 A | 7/1993 | Boswell |

(Continued)

FOREIGN PATENT DOCUMENTS

| | | |
|---|---|---|
| DE | 2900265 A1 | 7/1980 |
| JP | 61205510 U | 12/1986 |

(Continued)

OTHER PUBLICATIONS

Office action issued Jun. 26, 2009 in related U.S. Appl. No. 11/613,937, 7 pgs.

(Continued)

*Primary Examiner* — Corrine M McDermott
*Assistant Examiner* — Son Dang
(74) *Attorney, Agent, or Firm* — Lisa E. Winsor, Esq.

(57) ABSTRACT

The present invention provides a medical suturing device structured with a retrieval puncturing needle formed with through-hole; a retrieval member able to be inserted through through-hole; an insertion puncture needle formed with through-hole; a hollow tube that can be inserted through insertion through-hole, and the distal tip of which is formed into a deformable bent portion; and a suture that can be inserted through the inside of hollow tube. The retrieval member is structured with an annular engagement member that can be deformed into a straight shape, a rod member that is connected to annular engagement member, and a grip that is provided with a mark. The mark is furnished on hollow tube, such that when retrieval puncturing needle and insertion puncture needle are in a condition where mark and mark are facing each other, the upper supporter and lower supporter can be detachably attached.

14 Claims, 9 Drawing Sheets

(56) References Cited

U.S. PATENT DOCUMENTS

| | | | |
|---|---|---|---|
| 5,242,427 A | 9/1993 | Bilweis | |
| 5,251,873 A | 10/1993 | Atkinson et al. | |
| 5,281,237 A | 1/1994 | Gimpelson | |
| 5,330,488 A | 7/1994 | Goldrath | |
| 5,336,229 A | 8/1994 | Noda | |
| 5,336,231 A | 8/1994 | Adair | |
| 5,363,539 A | 11/1994 | Tisol | |
| 5,364,410 A | 11/1994 | Failla et al. | |
| 5,389,082 A | 2/1995 | Baugues et al. | |
| 5,391,182 A | 2/1995 | Chin | |
| 5,462,560 A | 10/1995 | Stevens | |
| 5,499,991 A | 3/1996 | Garman et al. | |
| 5,501,691 A * | 3/1996 | Goldrath | 606/148 |
| 5,531,699 A | 7/1996 | Tomba et al. | |
| 5,562,684 A | 10/1996 | Kammerer | |
| 5,626,590 A | 5/1997 | Wilk | |
| 5,643,295 A | 7/1997 | Yoon | |
| 5,653,716 A | 8/1997 | Malo et al. | |
| 5,665,096 A | 9/1997 | Yoon | |
| 5,681,333 A | 10/1997 | Burkhart et al. | |
| 5,722,981 A * | 3/1998 | Stevens | 606/148 |
| 5,728,109 A | 3/1998 | Schulze et al. | |
| 5,741,276 A | 4/1998 | Poloyko et al. | |
| 5,782,845 A | 7/1998 | Shewchuk | |
| 5,795,335 A | 8/1998 | Zinreich | |
| 5,817,108 A | 10/1998 | Poncet | |
| 5,817,111 A | 10/1998 | Riza | |
| 5,895,395 A | 4/1999 | Yeung | |
| 5,897,563 A | 4/1999 | Yoon et al. | |
| 5,921,993 A | 7/1999 | Yoon | |
| 5,938,668 A * | 8/1999 | Scirica et al. | 606/145 |
| 5,993,434 A | 11/1999 | Dev et al. | |
| 6,022,360 A | 2/2000 | Reimels et al. | |
| 6,036,700 A | 3/2000 | Stefanchik et al. | |
| 6,066,146 A | 5/2000 | Carroll et al. | |
| 6,110,183 A | 8/2000 | Cope | |
| 6,113,068 A | 9/2000 | Ryan | |
| 6,113,611 A | 9/2000 | Allen et al. | |
| RE36,974 E | 11/2000 | Bonutti | |
| 6,156,056 A | 12/2000 | Kearns et al. | |
| 6,451,024 B1 | 9/2002 | Thompson et al. | |
| 6,500,184 B1 | 12/2002 | Chan et al. | |
| 6,524,317 B1 | 2/2003 | Ritchart et al. | |
| 6,629,534 B1 | 10/2003 | St. Goar et al. | |
| 6,638,286 B1 | 10/2003 | Burbank et al. | |
| 6,699,263 B2 | 3/2004 | Cope | |
| 7,090,690 B2 | 8/2006 | Foerster et al. | |
| 7,306,613 B2 * | 12/2007 | Kawashima et al. | 606/148 |
| 7,320,693 B2 | 1/2008 | Pollack et al. | |
| 7,625,386 B2 | 12/2009 | Abe et al. | |
| 7,647,122 B2 | 1/2010 | Chan et al. | |
| 7,731,726 B2 | 6/2010 | Belhe et al. | |
| 7,918,868 B2 * | 4/2011 | Marshall et al. | 606/144 |
| 2002/0147456 A1 | 10/2002 | Diduch et al. | |
| 2003/0004523 A1 | 1/2003 | Chan et al. | |
| 2003/0109883 A1 * | 6/2003 | Matsuzaki et al. | 606/86 |
| 2004/0039442 A1 | 2/2004 | St. Goar et al. | |
| 2004/0122473 A1 | 6/2004 | Ewers et al. | |
| 2004/0249393 A1 | 12/2004 | Weisel et al. | |
| 2004/0249395 A1 | 12/2004 | Mikkaichi et al. | |
| 2005/0253033 A1 | 11/2005 | Mizukoshi et al. | |
| 2005/0288689 A1 * | 12/2005 | Kammerer et al. | 606/142 |
| 2006/0069398 A1 | 3/2006 | Suzuki et al. | |
| 2007/0118153 A1 | 5/2007 | Funamura et al. | |
| 2007/0179509 A1 | 8/2007 | Nagata et al. | |
| 2007/0282351 A1 | 12/2007 | Harada et al. | |
| 2007/0293876 A1 * | 12/2007 | Abe et al. | 606/144 |
| 2008/0200931 A1 | 8/2008 | Harada et al. | |
| 2008/0228204 A1 * | 9/2008 | Hamilton et al. | 606/148 |
| 2008/0243147 A1 * | 10/2008 | Hamilton et al. | 606/144 |
| 2008/0255591 A1 | 10/2008 | Harada et al. | |
| 2008/0269781 A1 | 10/2008 | Funamura et al. | |
| 2009/0088778 A1 | 4/2009 | Miyamoto et al. | |
| 2009/0163939 A1 | 6/2009 | Mabuchi et al. | |
| 2009/0318939 A1 | 12/2009 | Funamura et al. | |

FOREIGN PATENT DOCUMENTS

| | | |
|---|---|---|
| JP | 04226643 A | 8/1992 |
| JP | 05161655 A | 6/1993 |
| JP | 06024533 B2 | 4/1994 |
| JP | 06044511 U | 6/1994 |
| JP | 07328020 | 12/1995 |
| JP | 2002336262 A | 11/2002 |
| JP | 2005270332 A | 10/2005 |
| JP | 2006025932 | 2/2006 |
| JP | 2006025933 | 2/2006 |
| JP | 2006025934 | 2/2006 |
| JP | 2006151429 | 5/2006 |
| JP | 2004141646 A | 6/2010 |
| WO | 9421178 A1 | 9/1994 |
| WO | 9522932 A1 | 8/1995 |
| WO | 03065903 A1 | 8/2003 |
| WO | 2004006782 A1 | 1/2004 |
| WO | 2007018520 A1 | 2/2007 |

OTHER PUBLICATIONS

Response filed Sep. 22, 2009 to Office Action dated Jun. 26, 2009 from related U.S. Appl. No. 11/613,937, 7 pgs.

Office action issued Jan. 5, 2010 in related U.S. Appl. No. 11/613,937, 8 pgs.

* cited by examiner

MEDICAL SUTURING DEVICE

FIELD OF THE INVENTION

This application is a continuation of U.S. patent application Ser. No. 11/613,937, filed 12/20/2006, which has been abandon. The present invention generally relates to a medical suturing device for suturing a suture site in a patient's body.

BACKGROUND OF THE INVENTION

Conventionally, a medical suturing device has been used to anchor by suturing a suture site in a patient's body, particularly a suture site comprising the skin and internal organs. For example, fluid food and drinks, such as fluid food and nutrients, are supplied using a gastrostomy tube for those persons whose ability to ingest food from the mouth by their own strength has been reduced due to old age or illness; such a gastrostomy tube is attached by forming a hole in the patient's abdominal wall. In this case, the abdominal wall and stomach wall must be anchored using a medical suturing device in order to properly attach the gastrostomy tube, as shown for example in Japanese Kokai Patent Application No. Hei 5[1993] 161655 (JP5161655).

This medical suturing device is provided with two puncturing needles disposed in parallel while maintaining a gap, and when used for suturing, first the two puncturing needles are led to simultaneously puncture the patient's suture site. Then a suture is passed through one of the puncturing needles, while an internal needle, the distal tip of which is connected to a loop member structured from wire, is passed through the other puncturing needle, and the internal needle is drawn out of the puncturing needle in a condition where the loop member has grasped the suture. The two puncturing needles are then drawn out of the patient, and both ends of the suture projecting from the patient's body are tied together, thus accomplishing the suture. The distal tip of the puncturing needle through which the internal needle is inserted faces the side of the distal tip aperture formed in a bend, and by this means, when the internal needle is pressed within the puncturing needle, the loop member is extended laterally and projected outward, such that it can grasp the suture.

In the above described conventional medical suturing device, when the loop body approaches from below the side facing the distal tip aperture of the inserted puncture needle, the loop body and the suture become difficult to interlace so a reliable engagement is impossible. Therefore the distal tip of the puncturing needle in which the loop is to be inserted is bent such that the distal tip aperture faces sideways. Nevertheless, this has the problem of increasing the resistance during puncture and making the puncture difficult to perform, and it also inflicts pain on the patient. As a result, while the conventional medical suturing device has low puncture resistance, the problem remains of the impossibility of reliable engagement of the loop body and the suture. If the interval between the two puncturing needles of the above described conventional medical suturing device is set at a large valve, the size of the loop body has to be increased to match this interval. In this case, it becomes impossible to form a loop body of sufficient size unless a wide space is occupied within the organ. This results in the problem of the impossibility of reliable engagement of the loop body and the suture.

SUMMARY OF THE INVENTION

In one aspect of the present invention, a medical suturing device generally comprises a retrieval puncturing needle having a retrieval through-hole extending from a proximal end to a distal tip. A retrieval member that can be inserted through said retrieval through-hole of said retrieval puncturing needle has an annular engagement member which is elastically deformable into a straight shape and a rod member that is connected to said annular engagement member. An insertion puncture needle having a through-hole extending from a proximal end to a distal tip is disposed substantially parallel to said retrieval puncturing needle, maintaining a predetermined interval therebetween. A hollow tube that can be inserted within the through-hole of said insertion puncture needle comprises a distal tip portion having an arc shaped region elastically deformable into a straight shape. The suturing device also includes a suture that can be inserted into the aforementioned hollow tube.

Other features will be in part apparent and in part pointed out hereinafter.

BRIEF DESCRIPTION OF THE DRAWINGS

The present invention will be explained, by way of example only, with reference to the accompanying drawings in which.

Corresponding reference characters indicate corresponding parts throughout the drawings.

DETAILED DESCRIPTION OF THE DRAWINGS

Figure 1:
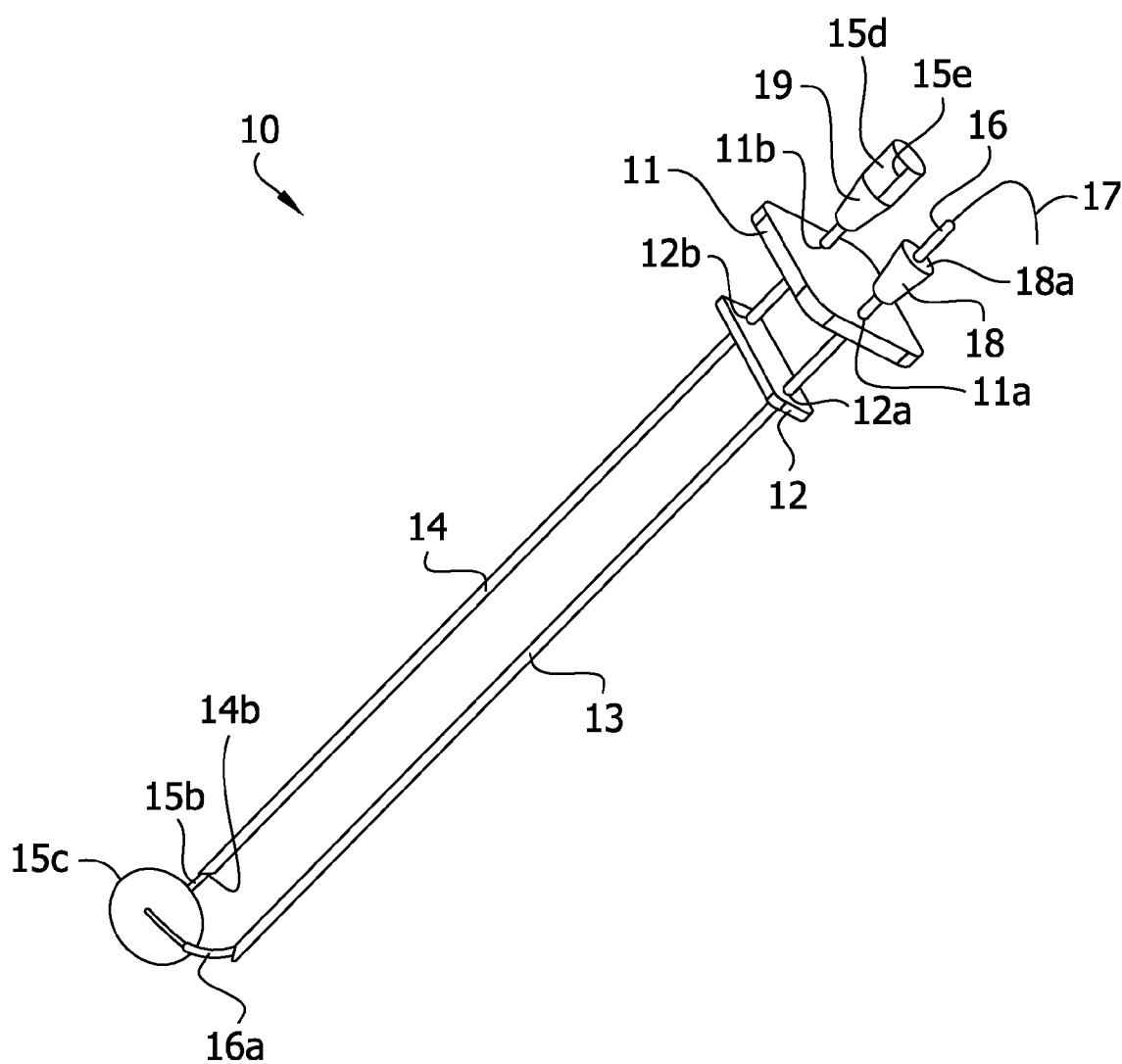
FIG. 1 is an oblique view showing the medical suturing device of an embodiment of the present invention.
Figure 2:
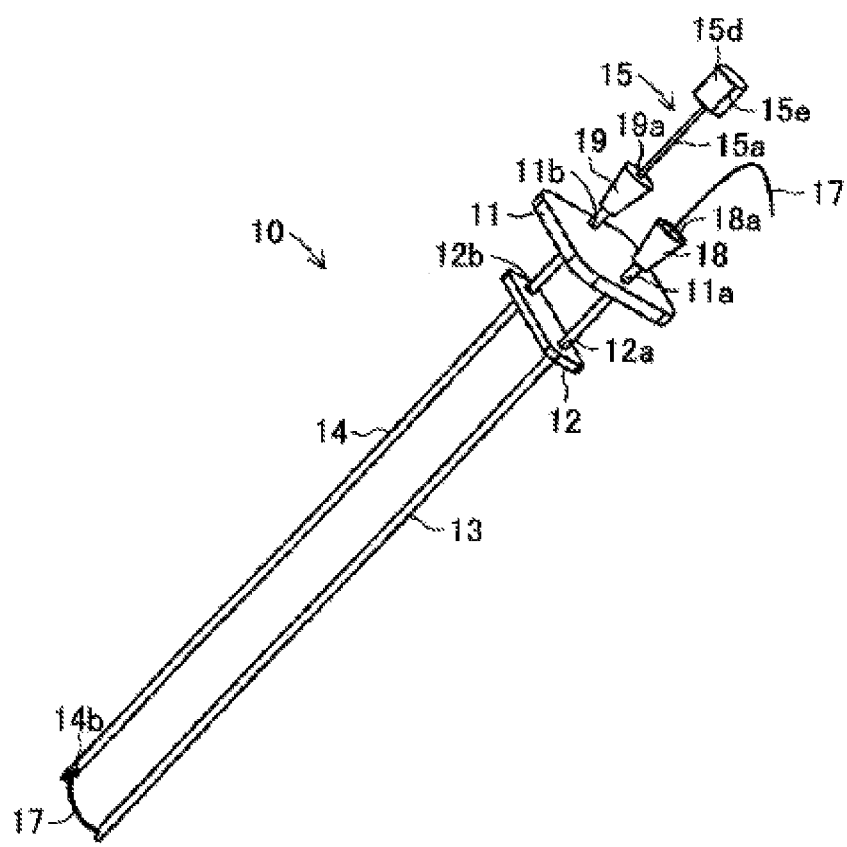
FIG. 2 is an oblique view showing the condition wherein the suture of the medical suturing device shown in FIG. 1 is engaged by the annular engagement member.

FIGS. 1 and 2 shows a medical suturing device 10 that pertains to the same working mode. The medical suturing device 10 is structured from a lower supporter 12 and upper supporter 11 that structure the invented supporter, a pair of puncturing needles comprising insertion puncture needle 13 and retrieval puncturing needle 14 that can be removably attached to upper supporter 11 and lower supporter 12, a retrieval member 15 that can be inserted through retrieval puncturing needle 14, a hollow tube 16 within insertion puncture needle 13, and suture 17 that can be inserted through hollow tube 16.

The upper supporter 11 and lower supporter 12 are respectively molded objects of resin materials, the upper supporter 11 is formed in a roughly square plate shape with corners cut away to form curved surfaces, and the lower supporter 12 is formed in a roughly rectangular plate shape with corners cut away to form curved surfaces. On both sides of upper supporter 11, the circular support holes 11a and 11b have been formed so as to sit astride the central point of upper supporter 11 at a fixed distance, and circular support holes 12a and 12b have been formed in both sides of lower supporter 12 along the longitudinal axis, maintaining the same interval as support holes 11a and 11b.

The insertion puncture needle 13 is structured as a tubular body of stainless steel, having a through-hole 13a (see FIG. 4) and a gripper 18 made of resin attached to a proximal end (upper end). The gripper 18 is formed as a cylinder for which the upper side has a major diameter and the lower side has a minor diameter, within which is formed a guide hole 18a that connects with through-hole 13a. The guide hole 18a is formed with a minor diameter on the lower part and a major diameter on the upper part along the peripheral surface of gripper 18, thus facilitating insertion of hollow tube 16 within through-hole 13a of insertion puncture needle 13 from the top of gripper 18. A distal tip (lower tip) of insertion puncture needle 13 is cut at a diagonal having a fixed angle with respect to the axis, and is formed so that a distal tip aperture 13b is visible from the side.

The through-hole extends from guide hole 18a of gripper 18 through to the distal tip aperture 13b. . The insertion puncture needle 13 is introduced through and supported by support hole 11a of upper supporter 11 and support hole 12a of lower supporter 12 in a condition where distal tip aperture 13b faces the direction of the central parts [i.e., the central axes] of upper supporter 11 and lower supporter 12. The upper supporter 11 supports the vicinity of the proximal end of insertion puncture needle 13, and lower supporter 12 maintains an interval with upper supporter 11 and supports a section of insertion puncture needle 13 slightly lower than the proximal end. In this case the attachment position of insertion puncture needle 13 in lower supporter 12 may be appropriately set according to the desired amount of projection of the lower part of insertion puncture needle 13 from lower supporter 12.

The retrieval puncturing needle 14 is structured as a cylinder of stainless steel, within which is formed a through-hole 14a, and to a proximal end of which is attached gripper 19 made of resin. The gripper 19 is formed as a cylinder for which the upper side has a major diameter and the lower side has a minor diameter, within which is formed an introduction hole 19a. A distal tip of retrieval puncturing needle 14 is cut in a diagonal direction so as to form a fixed angle facing the axial orientation, such that a distal tip aperture 14b is visible from the side.

The retrieval puncturing needle 14 is introduced through and supported by support hole 11b of upper supporter 11 and support hole 12b of lower supporter 12 in a condition where distal tip aperture 14b faces the direction of the central parts [i.e., the central axes] of upper supporter 11 and lower supporter 12. The upper supporter 11 supports the vicinity of the proximal end of retrieval puncturing needle 14, and lower supporter 12 maintains an interval with upper supporter 11 and supports a section of retrieval puncturing needle 14 slightly lower than the distal tip. In this case the attachment position of retrieval puncturing needle 14 in lower supporter 12 may be appropriately set according to the desired amount of projection of the lower part of retrieval puncturing needle 14 from lower supporter 12. The retrieval puncturing needle 14 is disposed so as to be substantially parallel to insertion puncture needle 13.

The retrieval member 15 is structured with a rod member 15a that is structured as a rod body of stainless steel, an annular engagement member 15c comprising a thin stainless steel wire anchored to a distal tip of rod member 15a by means of anchoring member 15b, and cylindrical grip 15d anchored to a proximal end of rod member 15a. In a condition where annular engagement member 15c is extended in a thin, long line, retrieval member 15 is introduced into introduction hole 19a of gripper 19 from the side of annular engagement member 15c, and by causing rod member 15a to move up and down within through-hole 14a of retrieval puncturing needle 14, the annular engagement member 15c is caused to emerge and retract from distal tip aperture 14b.

At this time, the operation is performed holding grip 15d. Also, the portion from introduction hole 19a of gripper 19 up to distal tip aperture 14b is structured with the through-hole. Also, grip 15d is structured by a molded article of resin material, and mark 15e, comprising a line that extends on its circumference extending axially over a predetermined portion, is displayed. The mark 15e is furnished on the periphery of grip 15d on a portion disposed along a line that is orthogonal to the hole portion of annular engagement member 15c.

The hollow tube 16 is structured with an elastic member comprising soft resin, with a molded thickness that permits insertion into insertion puncture needle 13 through through-hole 13a, and with the length set longer than insertion puncture needle 13. The distal tip 16a of hollow tube 16 is formed bent into an arc, but straightens to a straight line when introduced into through-hole 13a of insertion puncture needle 13. The parts other than distal tip 16a of hollow tube 16 are formed in a straight line, and a part on the proximal end periphery that corresponds to the arc shaped interior side of distal tip 16a displays mark 16b comprising a line that extends axially.

Therefore, retrieval member 15 is attached to retrieval puncturing needle 14, and hollow tube 16 is established within insertion puncture needle 13, mark 15e of grip 15d and mark 16b of hollow tube 16 are put in opposition, and the distal tip of hollow tube 16 projects from distal tip aperture 13b of insertion puncture needle 13 facing annular engagement member 15c projecting from distal tip aperture 14b of retrieval puncturing needle 14. Also, the suture 17 is structured by a thin thread comprising a resin material with a thickness allowing its passage through hollow tube 16.

The following statements describe the use of medical suturing device 10 having this structure for the case of suturing a patient's abdominal wall and stomach wall as an example. At first a condition exists where suture 17 and hollow tube 16 have been removed from insertion puncture needle 13. The annular engagement member 15c of retrieval member 15 and the lower portion of rod member 15a are inserted into retrieval puncturing needle 14. In this case, a condition exists where grip 15d is positioned above gripper 19 and the upper portion of rod member 15a is allowed to project above gripper 19, and annular engagement member 15c is positioned within retrieval puncturing needle 14. Then, in this condition, medical suturing device 10 is pushed into the skin surface of the patient's abdomen, and, as shown in FIG. 3 and FIG. 4, the insertion puncture needle 13 and retrieval puncturing needle 14 pierce into abdominal wall A and stomach wall B.

Figure 3:
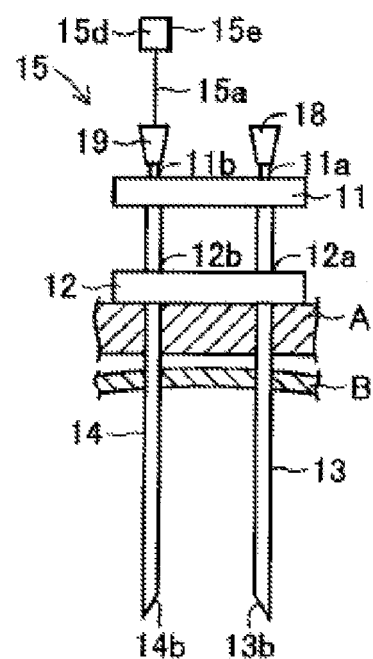
FIG. 3 is a cross section shown the condition wherein the medical suturing device is inserted into the abdomen of a patient.
Figure 4:
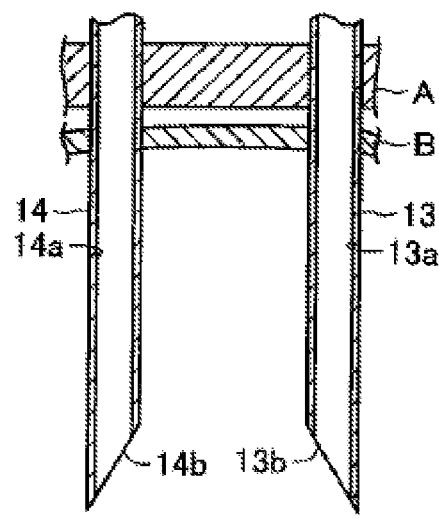
FIG. 4 is a cross sectional enlargement of the part of the medical suturing device of FIG. 3 that punctures the abdomen.
Figure 5:
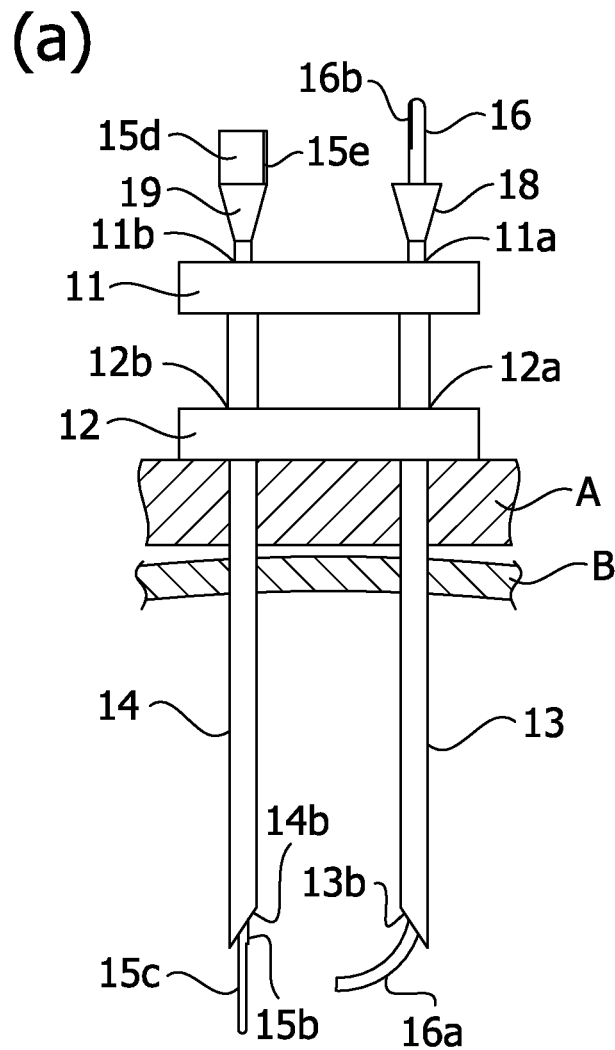
FIG. 5 is a cross section (a) showing a condition where the annular engagement member and hollow tube are projecting from the apex of the medical suturing device; a side view (b), showing the annular engagement member; and a side view (c) showing the hollow tube.
Figure 5:
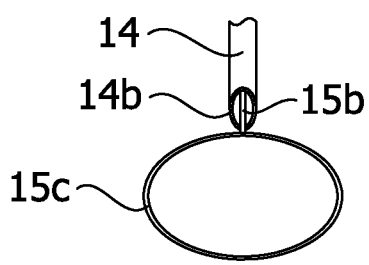
Figure 5:
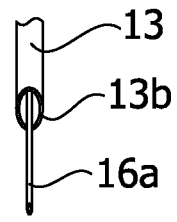

FIG. 3, as well as FIGS. 5, 7, 10, and 12 used in the following explanation, are drawings that schematically show medical suturing device 10, and the sizes and detailed forms, for example, differ from the medical suturing device 10 shown in FIG. 1 and FIG. 2. In this case, insertion puncture needle 13 and retrieval puncturing needle 14 are inserted until lower supporter 12 comes in contact with the skin surface of abdominal wall A, such that distal tip apertures 13b and 14b are positioned on the inside of stomach wall B. Then, mark 15e of grip 15d faces insertion puncture needle 13, and in this condition grip 15d is pushed down, and rod member 15a is pushed into through-hole 14a of retrieval puncturing needle 14. By this means, annular engagement member 15c is fed out to the exterior of retrieval puncturing needle 14 from distal tip aperture 14b, and the annular shape is restored. As shown in FIG. 5, it assumes a shape extending straight downward.

Figure 6:
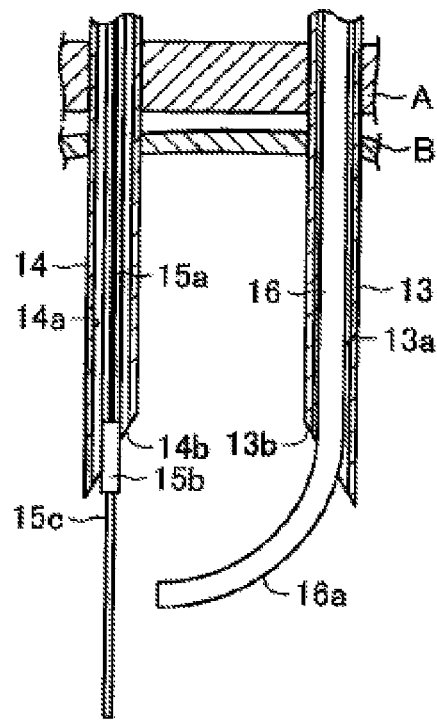
FIG. 6 is a cross section showing an enlargement of the section of the annular engagement member and hollow tube of FIG. 5.
Figure 7:
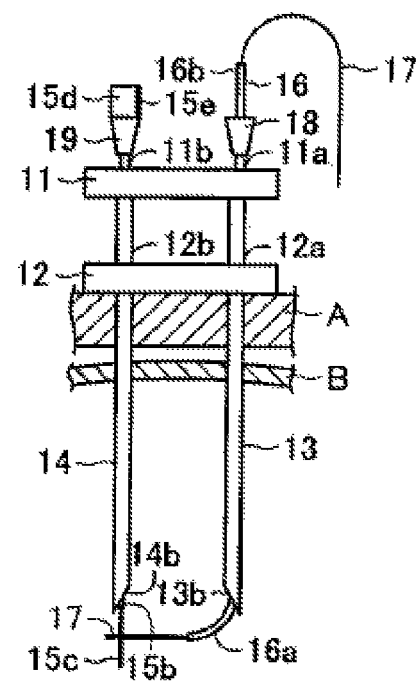
FIG. 7 is a cross section showing the condition where the suture projecting from the hollow tube enters within the annular engagement member.
Figure 8:
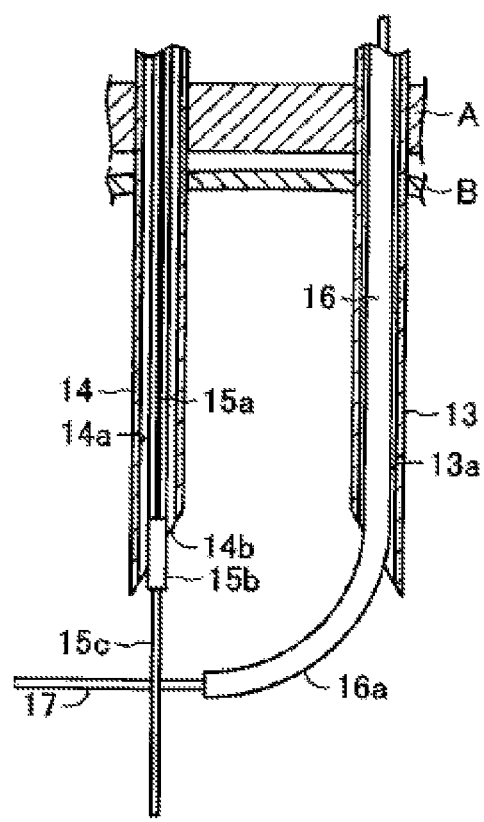
FIG. 8 is a cross sectional enlargement of the part of the suture projecting from the hollow tube and the annular engagement member of FIG. 7.
Figure 9:
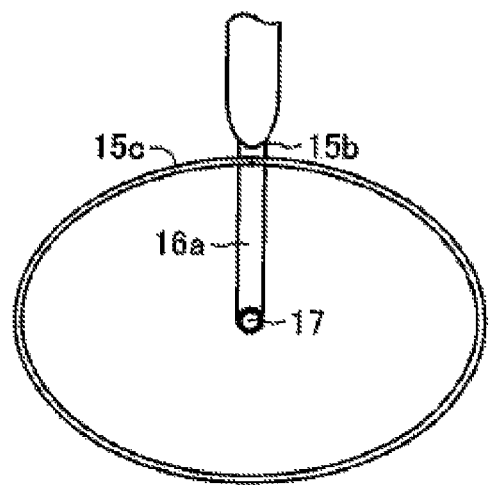
FIG. 9 is a side view showing a condition from the side of the part of the suture projecting from the hollow tube and the annular engagement member of FIG. 7.

Next, in a condition where the distal tip portion of suture 17 has been introduced into hollow tube 16, the hollow tube 16 together with the suture is introduced from guide hole 18a of gripper 18 into through-hole 13a of insertion puncture needle 13. By this means, distal tip 16a of hollow tube 16 is deformed into a straight line and progresses downward through through-hole 13a, until it extends outward from distal tip aperture 13b as shown in FIG. 6. At this time mark 16b of hollow tube 16 is faced toward mark 15e of grip 15d. By this means, distal tip 16a of hollow tube 16 is returned to its original arc shape, and faces toward the inside of annular engagement member 15c. Then, when suture 17 is introduced into hollow tube 16, the distal tip of suture 17 advances into annular engagement member 15c as shown in FIGS. 7-9.

Figure 10:
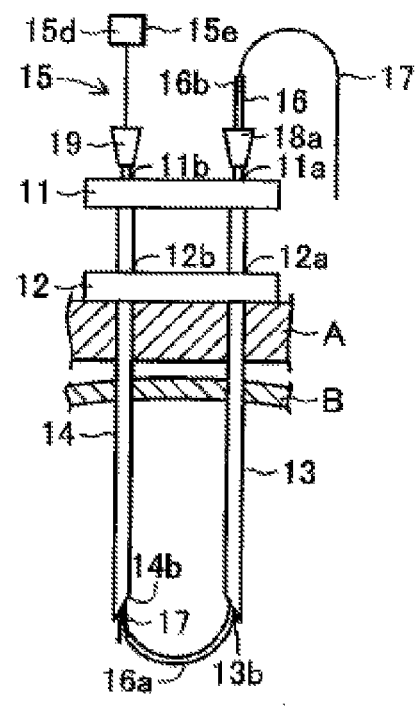
FIG. 10 is a cross section showing a condition where the suture is engaged by the annular engagement member.
Figure 11:
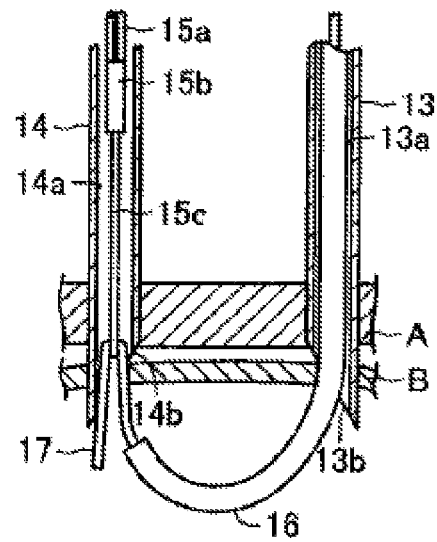
FIG. 11 is a cross section showing an enlargement of the part where the suture is engaged by the annular engagement member in FIG. 10.

Then, as shown in FIG. 10, the grip 15d is drawn upward, causing rod member 15a to project above gripper 19. By this means, annular engagement member 15c is drawn up into retrieval puncturing needle 14 and is stretched into a straight shape. Then, as shown in FIG. 11, the distal tip of suture 17 becomes engaged in annular engagement member 15c and enters into retrieval puncturing needle 14. In this condition, hollow tube 16 is pulled and drawn out of insertion puncture needle 13. Then medical suturing device 10 is pulled, and removed from the patient's body.

Figure 12:
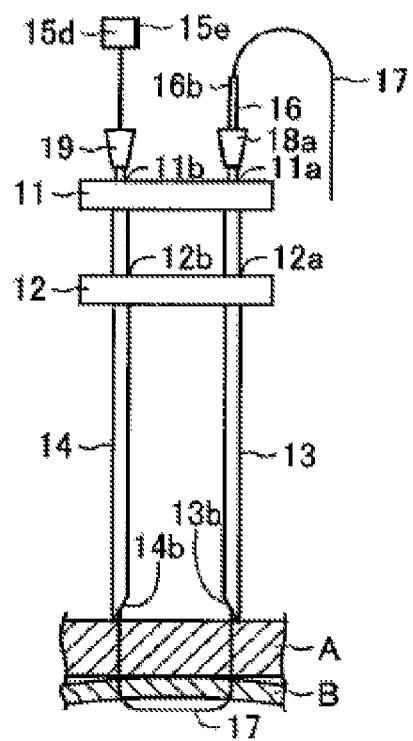
FIG. 12 is a cross section showing a condition where the medical suturing device is being removed from the abdomen.
Figure 13:
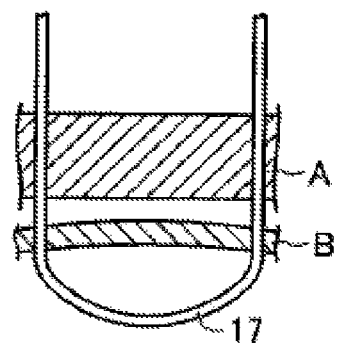
FIG. 13 is a cross section showing a condition where both ends of the suture have been cut.
Figure 14:
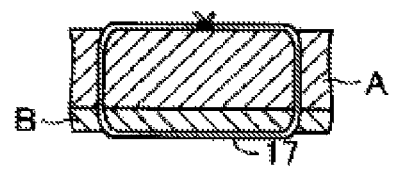
FIG. 14 is a cross section showing a condition where the suture is completed.

At this time, the distal tip of suture 17 is maintained in a condition of engagement within annular engagement member 15c. Therefore, when medical suturing device 10 is drawn out of the patient's body, suture 17, as shown in FIG. 12, connects stomach wall B to abdominal wall A while both ends are drawn out of the patient's body. Then, as shown in FIG. 13, the two ends of suture 17 that project outside the body are cut to form a predetermined length. The 2 cut ends of suture 17 are then knotted to form the sutured condition of FIG. 14, thus completing the process.

As described above, the medical suturing device 10 permits the deformation of annular engagement member 15c of retrieval member 15, so when retrieval member 15 is inserted inside retrieval puncturing needle 14 starting from annular engagement member 15c, the annular engagement member 15c assumes a straight shape and is moved within through-hole 14a, and assumes an annular shape when it is projected from distal tip aperture 14b of retrieval puncturing needle 14. The distal tip 16a of hollow tube 16 is formed with an arc shaped curved part that is able to deform into a straight line. Thus, when hollow tube 16 is inserted inside insertion puncture needle 13 starting from distal tip 16a, the distal tip 16a of hollow tube 16 assumes a straight shape and is moved within through-hole 13a, and bends into an arc shape when thrust out of distal tip aperture 13b of insertion puncture needle 13.

The mark 15e is provided on grip 15d of retrieval member 15, and mark 16b is provided on the periphery of the proximal end of hollow tube 16. In the condition where mark 15e of grip 15d faces mark 16b of hollow tube 16, and the retrieval member 15 is attached to retrieval puncturing needle 14, with the hollow tube 16 attached to insertion puncture needle 13, the annular shape of annular engagement member 15c projecting from distal tip aperture 14b of retrieval puncturing needle 14 faces insertion puncture needle 13, and distal tip 16a of hollow tube 16 projecting from distal tip aperture 13b of insertion puncture needle 13 extends toward annular engagement member 15c.

Thus when suture 17 is passed through hollow tube 16 in this condition, it becomes possible for the distal tip of suture 17 to extend inside the annular shape of annular engagement member 15c. Then, the withdrawal of retrieval member 15 in this condition from retrieval puncturing needle 14 enables engagement of suture 17 in annular engagement member 15c. Then, in this condition where suture 17 is engaged in annular engagement member 15c, the hollow tube 16 is withdrawn from insertion puncture needle 13 and both insertion puncture needle 13 and retrieval puncturing needle 14 are withdrawn from the patient's body, and both ends of suture 17 positioned outside the patient's body are knotted, thus making it possible to anchor stomach wall B to the abdominal wall A by a simple operation.

In this case, suture 17 is thrust outward from insertion puncture needle 13 in a condition of having been guided by hollow tube 16 bent into an arc shape and facing toward annular engagement member 15c, so the needle tips of insertion puncture needle 13 and retrieval puncturing needle 14 can face straight downward and can be given a tapered shape. Thus the needle resistance of insertion puncture needle 13 and retrieval puncturing needle 14 is reduced, making it possible for insertion puncture needle 13 and retrieval puncturing needle 14 to easily puncture the patient's body.

The insertion puncture needle 13 and retrieval puncturing needle 14 are attached to a support device comprising upper supporter 11 and lower supporter 12, which enables disposal of insertion puncture needle 13 and retrieval puncturing needle 14 in a suitable positional relationship, and simplification of the operation of insertion into the patient's body. The insertion puncture needle 13 and retrieval puncturing needle 14 are removably attachable to the support device, which makes it possible to use medical suturing device 10 many times while replacing one or the other needle according to conditions. The upper supporter 11 and lower supporter 12 can also be used as a gripping area to be held by the hand, which facilitates the operation of medical suturing device 10.

The medical suturing device pertaining to the present invention is not limited to the working mode described above, but can be implemented with suitable changes. For example, in the above described medical suturing device 10, only the distal tip 16a of hollow tube 16 was formed into a bent section with an arc shape, while the other portions were formed in a straight shape, but it is also possible for hollow tube 16 to be entirely formed in an arc shape. Essentially anything is permitted as long as, when distal tip 16a of hollow tube 16 is thrust out of distal tip aperture 13b of insertion puncture needle 13, distal tip 16a is extended toward annular engagement member 15c. By this means, the distal tip of suture 17 inserted into hollow tube 16 can be reliably advanced into annular engagement member 15c.

In the working mode described above, grip 15*d* was furnished with mark 15*e* as a position determining means, so as to determine the position of retrieval member 15, but other means besides a mark are possible as a position determining means. For example, it is possible to provide a projection and a cavity that engages with that projection at fixed parts of retrieval member 15 and retrieval puncturing needle 14, such that the projection and cavity will act as guides when retrieval member 15 is inserted into retrieval puncturing needle 14, such that retrieval member 15 will be facing in a fixed direction with regard to retrieval puncturing needle 14.

Again, in the working mode described above, hollow tube 16 was furnished with mark 16*b* as a position determining means, so as to determine the position of hollow tube 16, but other means besides a mark are possible as a position determining means. For example, it is possible to provide a projection and a cavity that engages with that projection at fixed parts of hollow tube 16 and insertion puncture needle 13, such that the projection and cavity will act as guides when hollow tube 16 is inserted into insertion puncture needle 13, such that hollow tube 16 will be facing in a fixed direction with regard to insertion puncture needle 13. By this means, the distal tip of suture 17 introduced into hollow tube 16 may be reliably engaged in annular engagement member 15*c*.

It is also possible to furnish a position determining means to fix the attachment positions of retrieval puncturing needle 14 and insertion puncture needle 13 with regard to the support device comprising upper supporter 11 and lower supporter 12; in this case a mark or guide section may be used as the position determining means. By this means it becomes possible to attach retrieval puncturing needle 14 and insertion puncture needle 13 in the support device so as to always have a fixed positional relationship, thus making the suture better. It is also possible to structure upper supporter 11 and lower supporter 12 by a single member that extends vertically, rather than as two separate plates; this makes it easy to hold the support device by hand, and facilitates operation during puncturing.

The shape of the needle tips for insertion puncture needle 13 and retrieval puncturing needle 14 is not limited to a shape where a tubular body is cut diagonally; rather, the distal tips may be furnished with approximately conical needle tips that gradually get narrower. It is also possible to suitably change the shape or materials, for example, of any part that structures the medical suturing device 10. Also, the medical suturing device 10 pertaining to the present invention is not limited to suturing abdominal wall A and stomach wall B, but may be used to suture any site within the body.

As can be seen from the above disclosure, at least one of the illustrated embodiments offers a medical suturing device that reduces puncture resistance and lessens the patient's pain, and that creates a reliable and proper suture.

The structural characteristics of the medical suturing device pertaining to at least one embodiment of the present invention are that it is furnished with a retrieval puncturing needle, in which a through-hole for retrieval is formed from the proximal end to the distal tip; a retrieval member that can be inserted through the retrieval through-hole of the retrieval puncturing needle, and that is furnished with an annular engagement member that has the elastic property of being deformable into a straight shape when caused to extend, and with a rod member that is connected to the annular engagement member; an insertion puncture needle in which a through-hole is formed from the proximal end to the distal tip, and that is disposed approximately parallel to the retrieval puncturing needle, maintaining a predetermined interval therebetween; a hollow tube that can be inserted within the through-hole of the insertion puncture needle, and for which at least the distal tip portion is formed with an arc shaped bent region having an elastic property of being deformable into a straight shape; and suture that can be inserted into the hollow tube.

The embodiment of the medical suturing device that has this structure provides that the annular engagement member of the retrieval member be elastic, so that it both deforms into a straight shape when it is extended, and returns to an annular shape when the extending force is removed. Therefore, when the retrieval member is inserted into the retrieval through-hole of the retrieval puncturing needle from the annular engagement member side, the annular engagement member assumes a straight shape and is moved within the retrieval through-hole, and then resumes its annular shape when it is projected from the distal tip of the retrieval puncturing needle, extending approximately straight downward. Also, the hollow tube is formed such that at least the distal tip portion is bent into an arc shape having elasticity to deform into a straight line.

Therefore, when the hollow tube is inserted from the distal tip portion into the through-hole of the insertion puncture needle, the distal tip portion of the hollow tube forms a straight shape and is moved within the through-hole, and when it is thrust out of the distal tip of the insertion puncturing needle it is bent into an arc shape. Accordingly, in a condition where the orientation of the distal tip of the hollow tube thrusting from the distal tip of the insertion puncture needle is adjusted so as to face the interior of the ring shape of the annular engagement member that is thrusting downward from the distal tip of the retrieval puncturing needle, it is possible, by passing a suture within the hollow tube, to extend the suture tip into the ring shape of the annular engagement member. It is then possible, by drawing the retrieval member in this condition out of the retrieval puncturing needle, to engage the suture in the annular engagement member. In this case, it is possible to reliably engage the annular engagement member and the suture, even if the interval between the insertion puncture needle and retrieval puncturing needle is large. Accordingly, it is possible to accommodate various organs having different internal spaces without changing the size of the annular engagement member.

More specifically, the operation in this case is first for the retrieval puncturing needle and insertion puncture needle to be held with a predetermined space between then and puncture the suture site from the surface of the patient's skin. Then the distal tip portion of the retrieval member is passed through the inside of the retrieval through-hole of the retrieval puncturing needle, and the annular engagement member that is structured on its apex is projected outside (i.e., inside the suture site). At the same time, the distal tip portion of the hollow tube is passed through the inside of the through-hole of the insertion puncture needle, its apex is compelled to face the annular engagement member and is then bent, and in this condition it is thrust outward, and the distal tip portion of the suture is passed through the hollow tube.

Then the retrieval member, in a condition where the distal tip of the suture is within the annular engagement member, is pulled toward the proximal end side of the retrieval puncturing needle, thus causing the suture to become engaged in the annular engagement member. Then, in a condition where the suture has been engaged in the annular engagement member, the hollow tube is withdrawn from the insertion puncture needle, and the retrieval puncturing needle and insertion puncture needle are withdrawn from the patient's suture site.

Then the suture site and the patient's skin layer can be anchored by knotting both ends of the suture positioned outside the patient's body.

In this way, with this medical suturing device, the annular engagement member of the retrieval member is formed into an annular shape when it is thrust below the distal tip of the retrieval member, while the suture, in the condition of having been guided by the hollow tube, is thrust out of the insertion puncture needle while being bent toward the annular engagement member. Thus it is possible for the distal tip apertures of both the retrieval puncturing needle and insertion puncture needle to be formed into sharp needle tips facing downward. By this means, because the puncture resistance of the retrieval puncturing needle and of the insertion puncture needle is reduced, it is possible for both puncturing needles to easily puncture the patient's suture site, and it is also possible to lessen the pain inflicted on the patient. This also allows reliable engagement of the suture in the annular engagement member. In one embodiment, the entire hollow tube can be formed into an arc shape, or only the distal tip portion can be formed into an arc shape.

Another structural characteristic of one embodiment of the medical suturing device is the furnishing of a position determining means such that when the retrieval member is introduced from its linearly extended annular engagement member side into the proximal end portion of the retrieval through-hole of the retrieval puncturing needle, the annular shape formed when the annular engagement member projects outwardly from the distal tip aperture of the retrieval puncturing needle is faced toward the insertion puncture needle.

The position determining means may be, for example, structured by putting a mark on a fixed portion on the periphery of the proximal end of the rod member of the retrieval member, and by furnishing a guide member such that when the retrieval member is inserted into the retrieval puncturing needle, the rod member is facing a predetermined direction. By this means, when the annular engagement member is thrust out of the distal tip of the retrieval member toward the outside, the ring shape of the annular engagement member will be facing the distal tip side of the insertion puncture needle, so the suture thrust out of the insertion puncture needle may more reliably engage in the annular engagement member.

Another structural characteristic of one embodiment of the medical suturing device is the furnishing of a position determining means such that when the hollow tube is inserted into the proximal end of the through-hole of the insertion puncture needle, and the distal tip portion projects outward from the distal tip aperture of the insertion puncture needle, the distal tip portion of the hollow tube will bend to extend toward the distal tip side of the retrieval puncturing needle.

In this case the position determining means may be structured by attaching a mark in a predetermined portion on the periphery of the proximal end of the hollow tube, thus providing a guide member so that when the hollow tube is inserted into the insertion puncture needle, the hollow tube will face a predetermined direction. By this means, the distal tip of the hollow tube can be compelled to face the annular engagement member that is thrust outward from the retrieval puncturing needle, and thus the distal tip of the suture inserted into the hollow tube may more reliably engage in the annular engagement member.

Another structural characteristic of one embodiment of the medical suturing device is that the retrieval puncturing needle and the insertion puncture needle are disposed in an approximately parallel fashion by their freely removable attachment to a support device. By this means, the retrieval puncturing needle and insertion puncture needle can be disposed in a proper positional relationship, thus making the operation of puncturing and insertion into the patient's suture site easier. The retrieval puncturing needle and insertion puncture needle are removably attached to the support device, which makes it possible to use a medical suturing device many times while replacing one or the other needle according to conditions. The support device can also be used as a gripping area to be held by the hand, which eliminates the need for the special provision of a grip on the retrieval puncturing needle and the insertion puncture needle. It is also possible to furnish a position determining means on the retrieval puncturing needle and the insertion puncture needle or protective device, in order to fix the positions for attachment of the retrieval puncturing needle and the insertion puncture needle with respect to the support device. This allows attachment of the retrieval puncturing needle and the insertion puncture needle to the support device so as to always be in a fixed positional relationship, which enables a better suturing operation.

Having described the illustrated embodiment(s) in detail, it will be apparent that modifications and variations are possible without departing from the scope of the invention defined in the appended claims.

When introducing elements of the present invention or the illustrated embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A suturing device for inserting a medical suture into a cavity in a patient's body and retrieving the suture from the body cavity, the device comprising:

an upper support;

a lower support spaced from the upper support, the lower support being fixed relative to the upper support;

an insertion puncture needle extending from the upper support and past the lower support to a distal end, said insertion puncture needle having a proximal end opposite the distal end and a through-hole extending along a centerline axis from the proximal end to an aperture at the distal end spaced from the lower support by a distance sufficient to position the aperture in the body cavity when the lower support contacts the patient's body;

a hollow tube having a size and shape consistent with inserting the hollow tube through the through-hole of the insertion puncture needle and a length sufficient to extend a distal portion of the hollow tube through the aperture of the insertion puncture needle, the distal portion having an arcuate undeflected shape and being sufficiently elastically deflectable that the distal portion of the hollow tube can straighten when withdrawn into the through-hole of the insertion puncture needle and return to the arcuate undeflected shape when extended from the insertion puncture needle through the aperture;

a retrieval puncture needle extending parallel to the insertion puncture needle from the upper support and past the lower support to a distal end needle, said retrieval puncture needle having a proximal end opposite the distal end and a through-hole extending along a centerline axis from the proximal end to an aperture at the distal end of the retrieval puncture needle spaced from the lower support by a distance sufficient to position the aperture of the retrieval puncture needle in the body cavity when the lower support contacts the patient's body; and a retrieval member having a size and shape consistent with inserting the retrieval member through the through-hole of the retrieval puncture needle and a length sufficient to extend an annular engagement element at the distal end of the retrieval member through the aperture of the retrieval puncture needle, the engagement element being sufficiently elastically deformable that the element can be collapse when withdrawn into the through-hole of the retrieval puncture needle and return to an annular shape when extended from the retrieval puncture needle through the aperture.

2. A suturing device as set forth in claim 1, wherein the aperture in the insertion puncture needle is oriented obliquely with respect to the centerline axis of the through-hole of the insertion puncture needle and generally facing the aperture in the retrieval puncture needle.

3. A suturing device as set forth in claim 2, wherein the aperture in the retrieval puncture needle is oriented obliquely with respect to the centerline axis of the through-hole of the retrieval puncture needle and generally facing the aperture in the insertion puncture needle.

4. A suturing device as set forth in claim 1, wherein the aperture in the retrieval puncture needle is oriented obliquely with respect to the centerline axis of the through-hole of the retrieval puncture needle and generally facing the aperture in the insertion puncture needle.

5. A suturing device as set forth in claim 1, wherein the hollow tube is rotatable within the through-hole of the insertion puncture needle and includes a position indicator indicating an orientation of the distal portion of the hollow tube.

6. A suturing device as set forth in claim 5, wherein the position indicator comprises a mark on the hollow tube.

7. A suturing device as set forth in claim 5, wherein the retrieval member is rotatable within the through-hole of the retrieval puncture needle and includes a position indicator indicating an orientation of the engagement element of the retrieval member.

8. A suturing device as set forth in claim 1, wherein the retrieval member is rotatable within the through-hole of the retrieval puncture needle and includes a position indicator indicating an orientation of the engagement element of the retrieval member.

9. A suturing device as set forth in claim 8, wherein the position indicator comprises a mark on the retrieval member.

10. A suturing device as set forth in claim 1, wherein the hollow tube includes a gripper for manipulating the hollow tube relative to the insertion puncture needle.

11. A suturing device as set forth in claim 10, wherein the retrieval member includes a gripper for manipulating the retrieval member relative to the retrieval puncture needle.

12. A suturing device as set forth in claim 1, wherein the retrieval member includes a gripper for manipulating the retrieval member relative to the retrieval puncture needle.

13. A suturing device as set forth in claim 1, wherein the aperture of the retrieval puncturing needle is beveled.

14. A suturing device as set forth in claim 1, wherein the insertion puncture needle and retrieval puncture needle extend proximally from the upper support.

* * * * *